United States Patent [19]

Proper et al.

[11] 4,272,782
[45] Jun. 9, 1981

[54] METHOD OF AND APPARATUS FOR ADJUSTING AN IMAGE INTENSIFIER CHAIN

[75] Inventors: Johannes Proper; Jacob Schuur; George L. A. Monte; Eduard P. Westerveld, all of Eindhoven, Netherlands

[73] Assignee: U.S. Philips Corporation, New York, N.Y.

[21] Appl. No.: 757,296

[22] Filed: Jan. 5, 1977

[30] Foreign Application Priority Data

Jan. 8, 1976 [NL] Netherlands ............ 7600142

[51] Int. Cl.³ .............. H04N 5/32; H01J 31/49; H01J 23/08; H04N 5/21
[52] U.S. Cl. .................... 358/111; 250/320; 250/333; 313/389; 315/5.34; 315/11; 358/167; 358/218; 358/227
[58] Field of Search .......... 358/111, 113, 167, 177, 358/218, 227, 110, 211; 313/365, 388, 389; 315/5.34, 10, 11; 250/320, 321, 213, 333

[56] References Cited

U.S. PATENT DOCUMENTS

3,894,181  7/1975  Mistretta et al. ............ 358/111

*Primary Examiner*—Robert L. Griffin
*Assistant Examiner*—Edward L. Coles
*Attorney, Agent, or Firm*—Thomas A. Briody; Robert T. Mayer; Jack E. Haken

[57] ABSTRACT

The light which is emitted from the output screen of an image intensifier and passed through a subsequent output objective, is converted into an electrical signal by means of a photomultiplier tube or an image pick-up tube. The noise or modulation content of the electrical signal are measured. An optimum adjustment of the focussing position of the output objective and the magnitude of the focussing voltage applied to the imge intensifier, cause the noise or modulation content to attain an extreme value, e.g. a maximum. The focussing voltage and the focussing position of the output objective are iteratively adjusted.

22 Claims, 6 Drawing Figures

METHOD OF AND APPARATUS FOR ADJUSTING AN IMAGE INTENSIFIER CHAIN

The invention relates to a method of adjusting an image intensifier chain in which an optimum adjustment is pursued, at least in respect of a focussing voltage applied to an image intensifier, while exposing the input screen of the image intensifier to input radiation. The invention also relates to apparatus for carrying out said method. Such a method and apparatus can be employed in systems in which the input radiation is X-radiation, gamma radiation, infra-red or visible optical radiation as in, for example, low-light-level systems. The determination of an optimum adjustment of a focussing voltage is usually effected by a purely subjective evaluation. In an X-ray system, this purpose is achieved by the use of a phantom arranged between an X-ray source and the image intensifier, and the intensifier image is visually evaluated. The optimization of an image of the phantom by adjustment of the focussing voltage of the image intensifier, is often performed in a room which is at least partly darkened, and this is disturbing for the user. The ultimate result of such an adjustment of the focussing voltage is greatly dependent on the powers of observation and on the experience of the person performing the adjustment. As a result, the adjustment of the image intensifier chain in practice will frequently depart from the optimum.

The invention has for an object to provide an improved method and apparatus whereby an image intensifier chain can be quickly and objective adjusted.

According to the invention, a method of adjusting a device of the kind set forth is characterized in that light originating from at least a part of the output screen of the image intensifier is converted into an electrical measuring signal, a difference between the measuring signal and a reference value is sensed and the focussing voltage is adjusted until said difference attains an extreme value.

In most contemporary X-ray systems, the light emitted through the exit window of the image intensifier is directed, via a lens system which comprises at least an output objective, onto an image pick-up tube or a photographic camera. The search for an optimum adjustment of the focussing voltage of the image intensifier and an optimum focussing position for the output objective, utilizing a subjective evaluation of the image of a phantom, is a time-consuming procedure which can be performed only by skilled and experienced personnel. Consequently, a method embodying the invention where an optimum adjustment is iteratively persued in respect of the focussing voltage of the image intensifier and in respect of the focussing position of an output objective, is characterized in that the difference between the measuring signal and the reference value is increased to an extreme value during each iteration. The use of this method reduces the amount of adjustment of the image intensifier chain needed to attain an optimal focus condition to a short series of operations so that the time required for the adjustment is substantially reduced. The adjustment obtained is reproducible, because a subjective evaluation has been replaced by an objective measurement. Therefore, the adjustment can be performed by less experienced personnel.

In a preferred method embodying the invention a noise signal is filtered from the measuring signal and adjustment is carried out until the absolute amplitude is maximum. The proposed method utilizes the quantum behaviour of input radiation, e.g. X-radiation. When uniform illumination received by the input screen of the image intensifier is intensified and relayed onto a display screen arranged beyond the output objective, it can be shown that the quantum behaviour of the input radiation will give rise to a maximum of noise in the image formed on the display screen when a correct focus adjustment of the image intensifier and of the output objective has been made. Any deviation from an optimally focussed image will give rise to an averaging of the noise. In a further method embodying the invention the input radiation is modulated as a function of location and/or of time and the light output thus produced is converted into a measuring signal which is modulated as a function of time. The modulation of the input radiation as a function of location and of time can be simply realized by causing a normally present graticule (e.g. in the case of X-radiation a grid for attenuating scattered radiation, such as a Potter-Bucky grid) to be movably arranged in front of the image intensifier and to perform a vibratory motion. The amount of light emitted by the output screen of the image intensifier is sensed and measured at one point. On the basis of this measurement a determination can be made as to whether the transmission of the modulated input signal through the image intensifier and the basic objective is optimal or not. The image transmission can alternatively be selectively obscured by a stationary graticule or grid in front of the image intensifier. A suitable detector, for example, an image pick-up tube, measures the light emitted by a series of adjacent locations on the output screen is measured. The stationary graticule modulates the input radiation with a spatial function. During the scanning of a series of adjacent points on the image pick-up tube this function is converted into a function of the time which is easier to process electronically.

In a preferred embodiment of a device for carrying out the invention the device comprises at least an image selector, photo-electric means, and a measuring instrument. The image selector includes a lens system having a focal point which is arranged to coincide with an opaque wall forming part of said image selector. At least one aperture is present in said wall which is arranged between the lens system and the photo-electric means. Such an arrangement can be easy to use and low in both initial and maintenance cost. It has been found to be useful to arrange the opaque wall and the associated photo-electric means to be rotatable about the optical axis of the lens system. Thus, after such a rotation, light emitted by a further portion of the output screen can be selected by said aperture and converted into a corresponding electrical measuring signal by the photo-electric means. If for the same adjustment of the focussing voltage and of the output objective, the difference between the last mentioned measuring signal and the reference corresponding to the measurement no longer exhibits an extreme value, a lack of coincidence between the optical axes of the image intensifer and the output objective is indicated.

In a further preferred embodiment of a device for carrying out the invention the device comprises an image pick-up tube, a non-linear amplifier and an integrator connected thereto. The use of an image pick-up tube for carrying out the invention can be convenient, because such a pick-up tube is already present in many X-ray systems. For the determination of a quantitative value of the noise, measured over a given surface area of the image or over a given period of time, the absolute value of the noise amplitude must always be used; otherwise averaging will occur during integration. To achieve this, the amplitude of the noise is amplified non-linearly while using the foregoing method.

Figure 1:
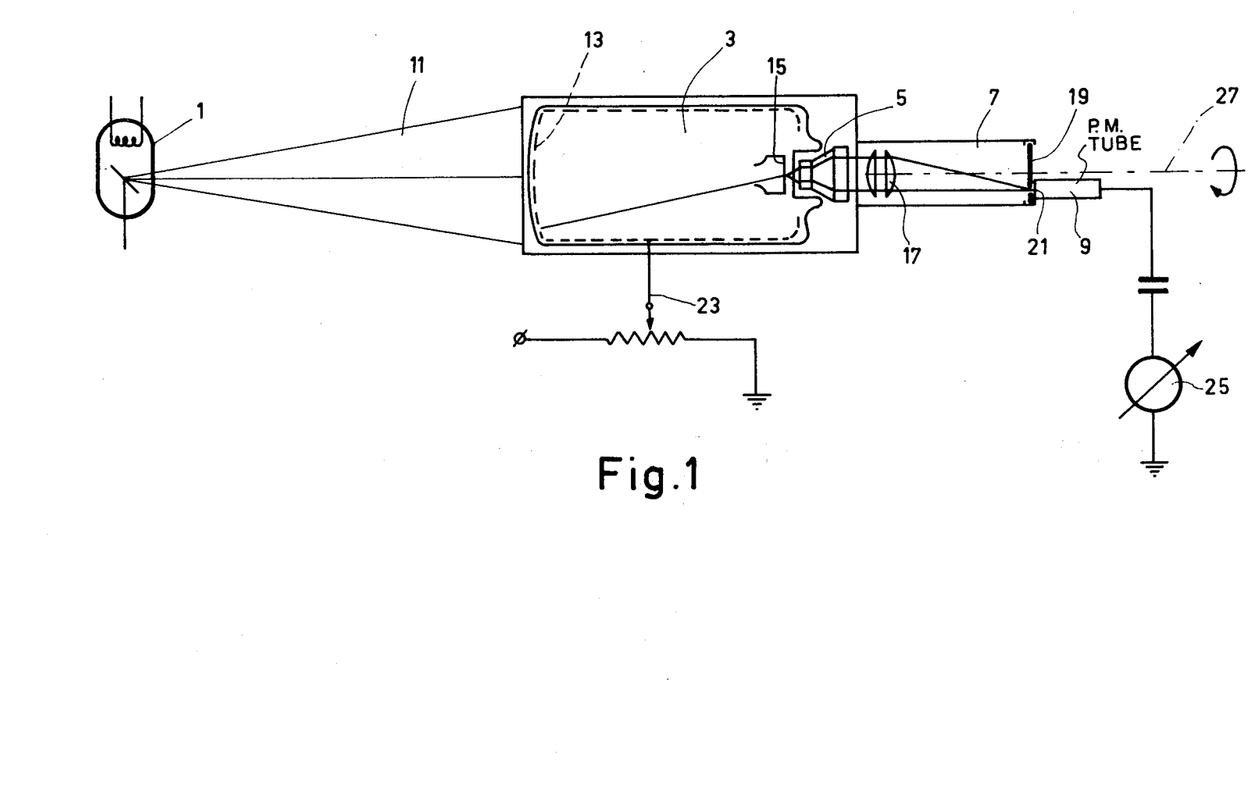
FIG. 1 is a schematic diagram of an X-ray system and apparatus for adjusting an image intensifier chain, using a method embodying the invention.

The schematic diagram of FIG. 1 shows an X-ray tube 1, an image intensifier 3, an output objective 5, an image selector 7 and a photomultiplier tube 9. The radiation 11 generated by the X-ray tube 1 is incident on an input screen 13. The electrons released from the input screen 13 cause fluorescence to occur at corresponding points on an output screen 15. The image selector 7 comprises a lens system 17 and a rear wall 19 in which an aperture 21 is provided. The distance between the lens system 17 and the rear wall is made equal to the focal distance of the lens system 17. When the magnitude of the focussing voltage 23 and the focussing position of the output objective 5 have been correctly adjusted, a well-focussed image of the radiation image incident on the input screen 13, will be produced on the rear wall 19. The position of the aperture 21 determines the region on the output screen 15 from which the emitted light is measured by the photomultiplier tube 9. This region will emit a quantity of light determined by the amount of excitation applied to a corresponding region of the input screen 13 by incident X-radiation 11. The light transmitted by the aperture 21 is converted into an electrical signal by the photomultiplier tube 9. The electrical signal will consist of a direct voltage component and an alternating voltage component. The alternating voltage component is caused by the quantized nature of the incident X-radiation 11 and is a noise signal. The instantaneous amplitude of the noise signal is measured by means of an alternating voltage meter 25. The value of the noise signal is at a maximum when the correct focussing voltage 23 and the correct focussing position for the output objective 5 have been attained by adjustment. If the adjustment is not optimum, then in addition to the noise content of the electrical signal originating from the selected region of the input screen 13, at least a part of the noise generated in the surrounding region will also be measured. This will take the form of an integration of noise as a function of the location, and will result in a smaller deflection on the alternating voltage meter 25.

The image selector 7 is arranged to be rotatable about the optical axis 27 which is common to the lens system 17, the output objective 5 and the image intensifier 3.

The preceding adjustment can thus be checked using the noise signal from other regions of the input screen 13. Using the same focussing voltage 23 and the same focussing position for the output objective 5, the measured noise signal must be at a maximum. If the optical axes of the image intensifier 3 and the output objective 5 do not coincide, the image formed on the rear wall 19 will not be uniformly focussed, and different optimal adjustments will need to be applied to the focussing voltage 23 and to the output objective 5 when the position of the aperture 21 is changed.

Figure 2A:
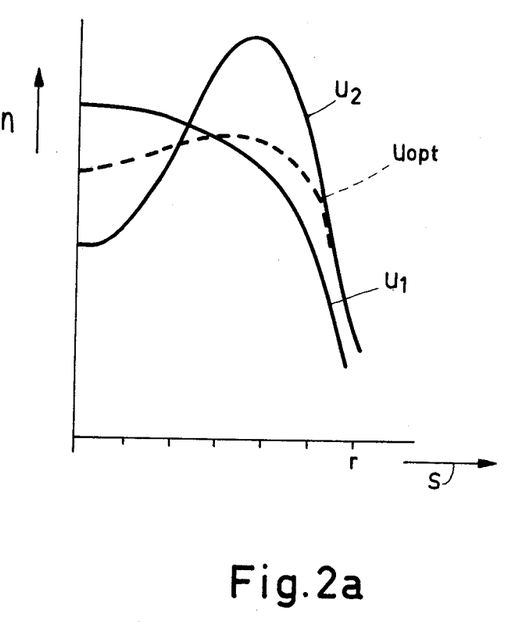
FIG. 2a is a graph showing the resolution over the output screen of an image intensifer as a function of the focussing voltage as a parameter.

In the graph shown in FIG. 2a the distance S from the optical axis 27 of the image intensifier 3 of FIG. 1 is plotted along the horizontal axis, r being the radius of the output screen 15 of the image intensifier 3. The number of lines n, for example, per cm length, which can just be resolved, is plotted along the vertical axis. The graph shows three curves, based on a stepwise variation of the focussing voltage U as the parameter, each representing the number n of lines per cm which can just be resolved as a function of the distance s from the optical axis 27. Depending on the manner of use of the image intensifier 3, for example, whether the whole of the image surface area or only the central portion thereof are to be employed, an appropriate optimum focussing voltage Uopt will be called for. By the conversion of the amount of light which is emitted by each of a plurality of different regions of the output screen located at different distances from the optical axis, into corresponding electrical signals, and transforming the set of signals into one value which is representative of a given operating status of the image intensifier 3, an optimum focussing voltage Uopt can be found. The transformation into one representative value can be effected electronically; however the assignment of a weighting factor to each signal can be effected mechanically and the addition electronically. In the latter case the spatial distribution of the locations from which the emitted light is measured, is determined statistically.

Figure 2B:
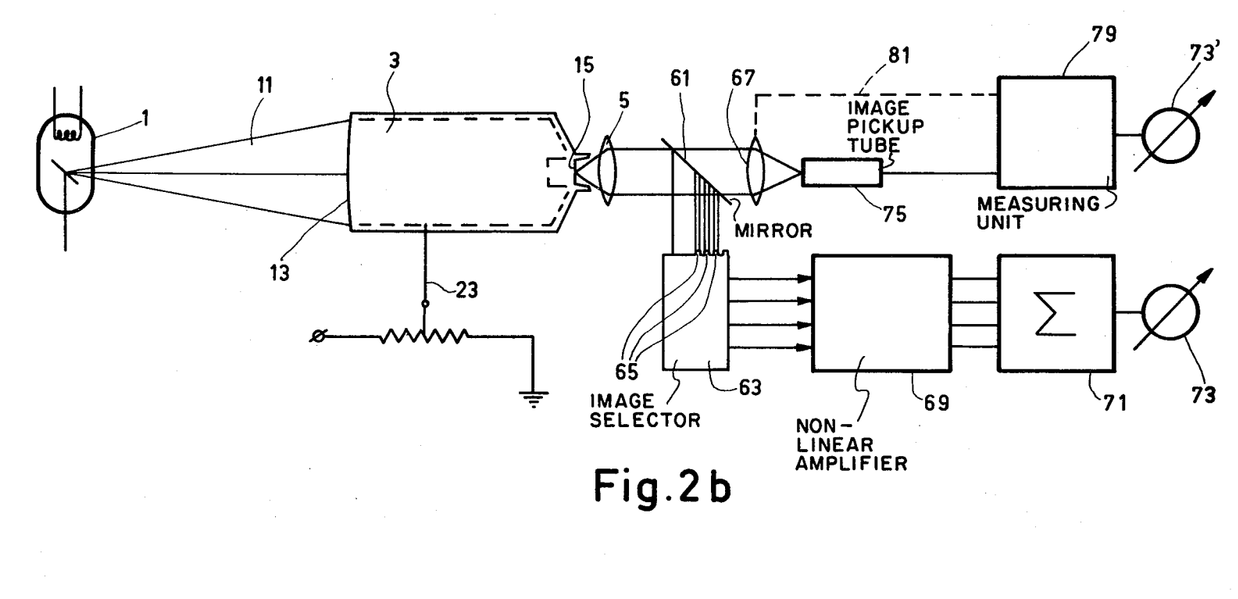
FIG. 2b shows an embodiment of an image selector wherein an optimum resolution can be obtained throughout substantially the entire output screen of the image intensifier.

An arrangement whereby the described method of measurement can be realized is shown in FIG. 2b. The light emitted by the output screen 15 of the image intensifier 3 is directed, by the output objective 5 and a partially transmissive mirror 61, to an image selector 63. Part of the light incident on the image selector 63 is transmitted by a plurality of apertures 65 and is respectively converted into corresponding electrical signals in the described manner. The signals are amplified by corresponding channels in a non-linear amplifier assembly 69 and are summed by an adder 71. The magnitude of the summation signal obtained by means of the adder 71 is indicated by an indicator 73. When both the focussing voltage 23 and the focussing position of the output objective 5 are variables to be adjusted, it is advantageous to employ an iterative process of adjustment in which for each adjustment step of a first variable, the other variable is adjusted until the deflection of the indicator 73 is a maximum, the stepwise adjustment of the first variable being continued until the highest maximum deflection of the indicator 73 is attained. Such an optimum adjustment of the image intensifier chain can be achieved after relatively few iterative steps.

The light transmitted by the partially transmissive mirror 61 is projected onto the photo-sensitive layer of an image pick-up tube 75 via a camera lens 67. A signal originating from the image pick-up tube 75 is processed by a measuring unit 79 described hereinafter. The output of the measuring unit 79 is connected to an indicator 73' which displays a deflection dependent on the magnitude of the signal originating from the image pick-up tube 75. The deflection of the indicator 73' is made maximum by displacement of the camera lens 67 in the correct direction. Automatic adjustment could be realized by means of a feedback control link 81 from the measuring unit 79 to the camera lens 67.

If the camera lens 67 and the output objective 5 are arranged to form a tandem lens system, in which the distance between the lenses 5 and 67 is fixed, the entire image intensifier chain, namely the focussing voltage 23 and the position of the tandem lens system, can be quickly adjusted by means of the image pick-up tube 75. This adjustment can be effected semi-automatically, by varying one variable manually, for example the position of the tandem lens system, while the other variable, in this case the focussing voltage 23, is automatically adjusted to an optimum value, by means of a feedback control, for each manually set position of the tandem lens system.

Figure 3:
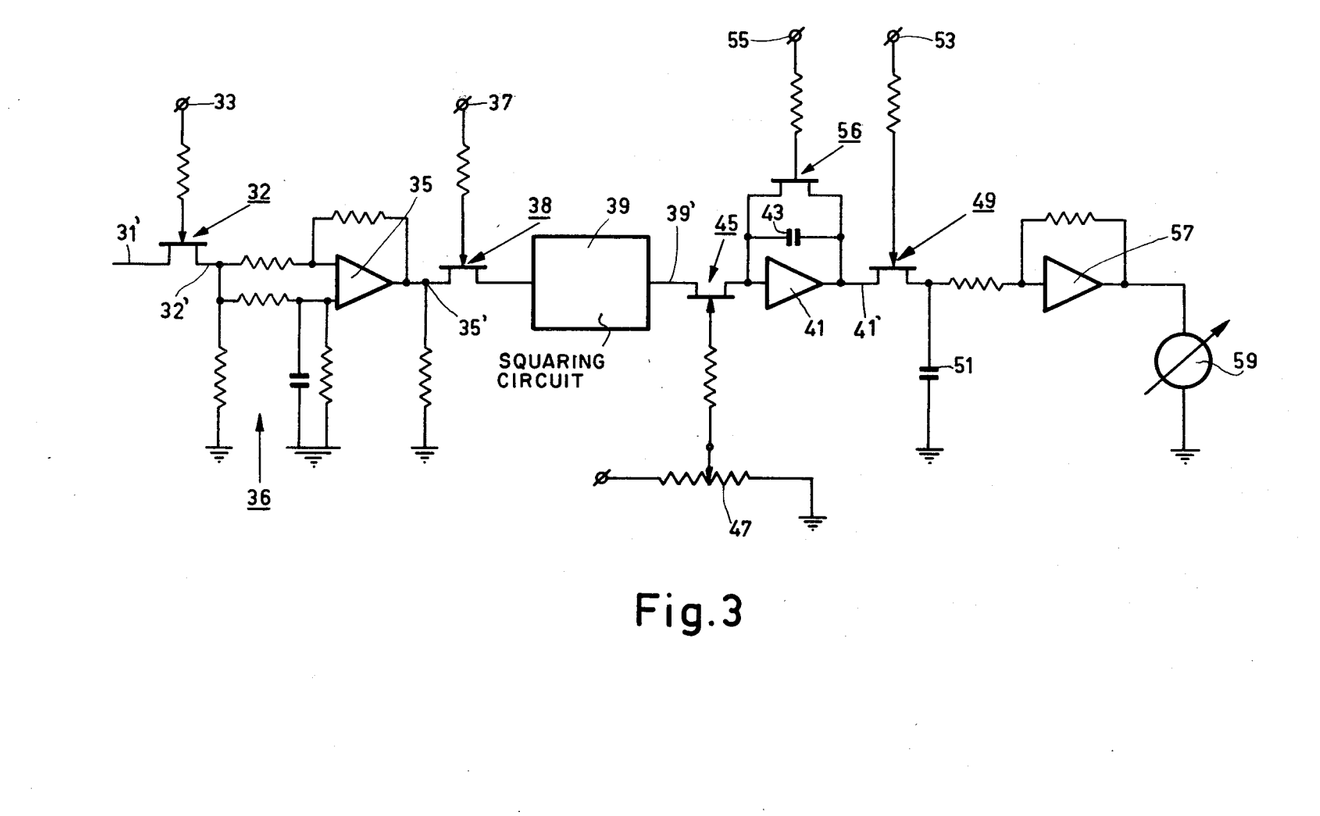
FIG. 3 shows schematically a circuit for determining the noise content of a signal originating from a television circuit.
Figure 4:
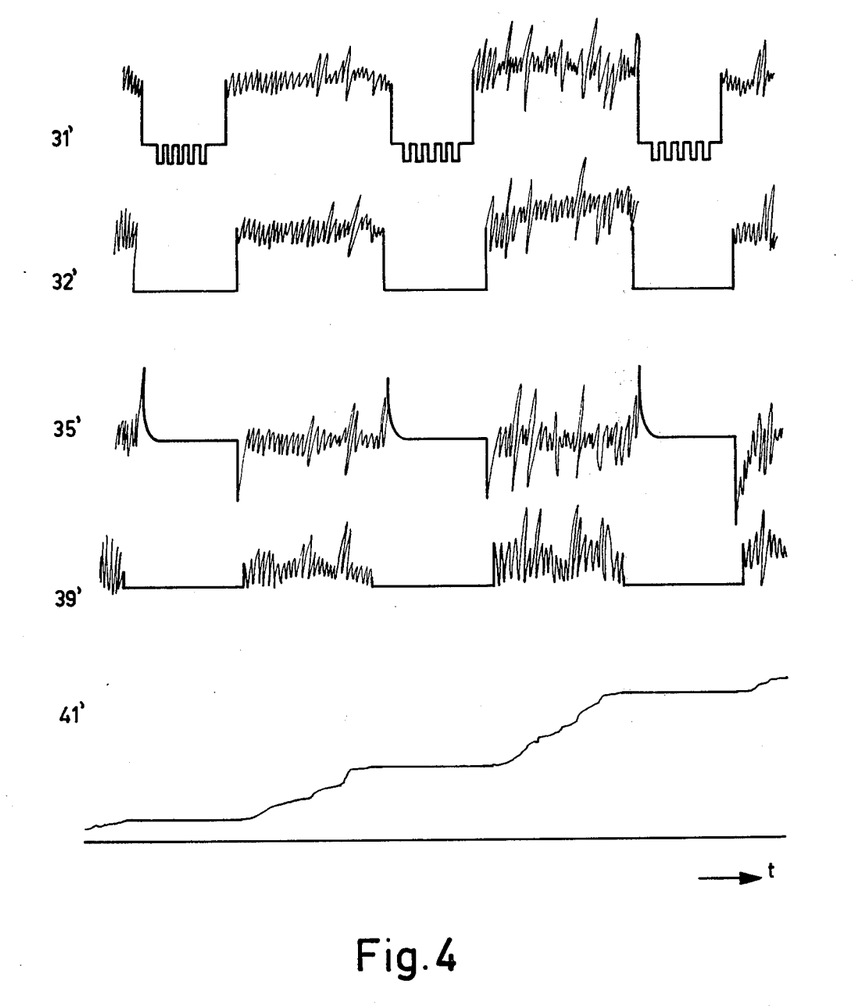
FIG. 4 shows various waveforms occurring in the circuit shown in FIG. 3.

FIG. 3 shows a schematic circuit for the measuring unit 79 whereby the noise content of a signal 31' originating from a television circuit (not shown) is determined. The waveforms of the signal 31' and of other signals denoted by an accent, which are present at various points in the circuit, are shown in FIG. 4. In order to separate the desired signal from synchronization pulses picked up from other parts of the television circuit, the transistor 32 is rendered non-conductive during the relevant periods by means of a suppression signal which is derived from the television circuit and which is applied to the input 33. The amplifier 35 in conjunction with an RC-network 36, constitutes a high-pass filter which filters the direct voltage component from the signal 32' passed by the transistor 32. The filtered signal 35' contains spikes at the beginning and end of the scanning line due to the corresponding steep edges of the signal 32'. The said spikes are clipped by a switching signal which is applied to the input 37 of the transistor 38. The amplitude of the remaining signal is raised to the power two by a squaring circuit 39. The output signal 39' is integrated by an integrator which consists of an amplifier 41, a capacitor 43 and a transistor 45 which acts as a resistor whose resistance is adjusted by means of a potentiometer 47. The integrated value 41' is read after the termination of each television frame. To perform this operation, the transistor 49 is rendered conductive by means of a read-out signal which is applied to the input 53. The capacitors 51 and 43 are thereby effectively connected in parallel and are charged to the same potential difference which is relayed via an amplifier 57, and indicated by a measuring instrument 59.

In order to reduce any disturbance of the result of the completed integration by the previous integration, as far as possible, the capacitance of the capacitor 43 is chosen so that it is many times larger (e.g. by a factor of 10-100) than that of the capacitor 51.

As soon as the transistor 49 is turned off at the end of the read-out signal applied to 53, the capacitor 43 is discharged via the transistor 55 which is rendered conductive for this purpose by means of a reset signal applied to the input 56; subsequently, a new measurement can commence.

Figure 5:
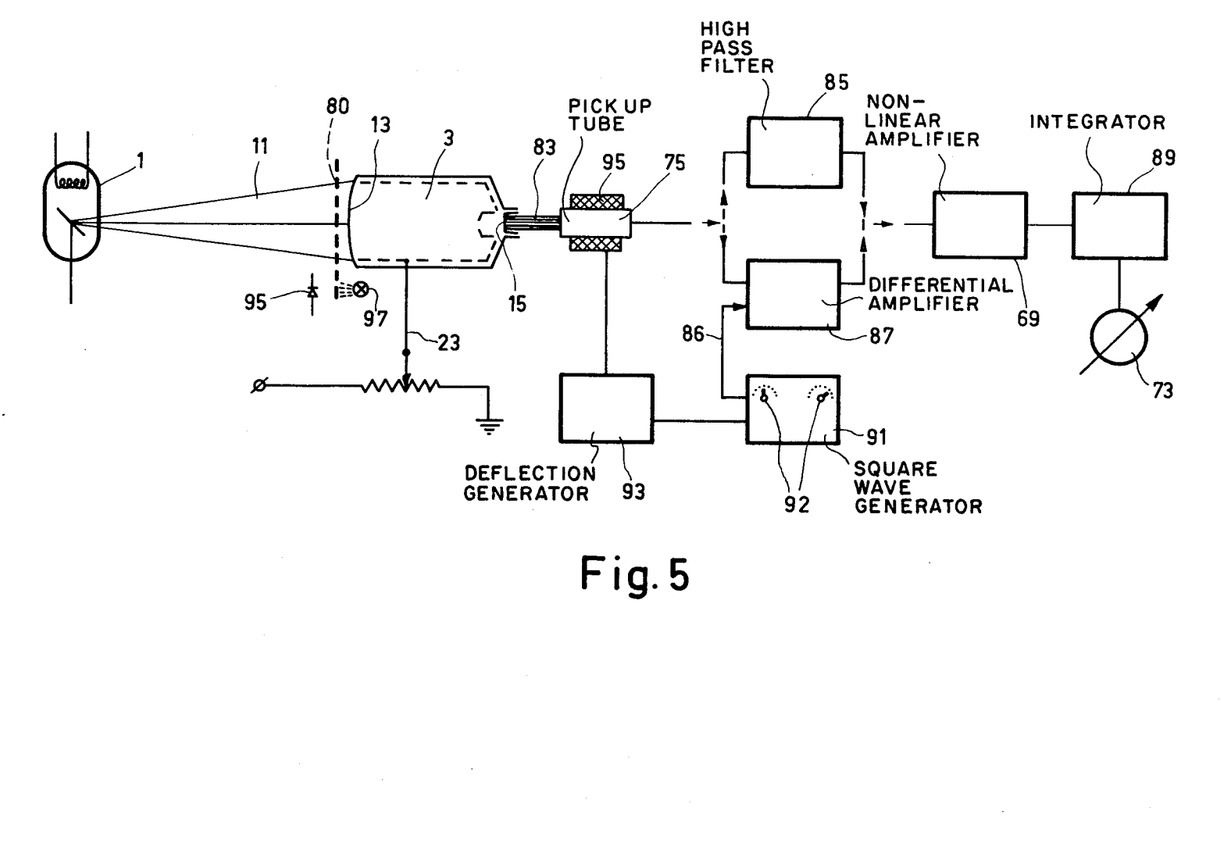
FIG. 5 illustrates two embodiments of a device for adjusting an image intensifier chain, the same modulated input signal being used for each embodiment.

FIG. 5 shows alternative forms of an arrangement in which the image intensifier chain is adjusted using a modulated input signal. The radiation 11 produced by the X-ray tube 1 is partly intercepted by a graticule or grid 80 which is arranged in front of the image intensifier 3. A grid 80 of this kind e.g. a Potter-Bucky grid is already present in many X-ray systems for intercepting scattered radiation. The X-radiation incident on the input screen 13 is thus modulated as a function of location. The light emitted by the output screen 15 is applied to a pickup tube 75 via a fibre-optical system 83. The signal read by the pick-up tube 75 is substantially a rectangular waveform as a result of the grid 80, arranged in front of the image intensifier 3. In the alternate forms of the arrangement, the signal is applied to a high-pass filter 85 or to a differential amplifier 87. The output signal of the filter 85 or the amplifier 87 is applied to a non-linear amplifier 69, the output signal of which is integrated by an integrator 89.

The differential amplifier 87 receives a reference signal 86 generated by a square-wave generator 91. The frequency of the square-wave voltage 86 is dependent on the spatial construction of the graticule or grid 80 and on the scanning frequency of the image pick-up tube 75. Data relevant to the spatial construction of the graticule or grid 80 is selected by control knobs 92. The deflection voltage which the deflection generator 93 applies to the deflection unit 95 is also fed to the square-wave generator 91. A suitable synchronization between the reference signal 86 and the signal read from the image pick-up tube 75, can thus be achieved. In this this alternative, the amplified and integrated output signal of the differential amplifier 87 should cause a minimum deflection of the indicator 73 when the adjustment of the image intensifier chain is optimal.

In the other alternative form of the arrangement, the high-pass filter 85 only allows the passage of frequencies which are higher than a cut off frequency which is determined by the spatial construction of the graticule or grid 80 and by the scanning frequency of the image pick-up tube 75. The amplified and integrated output signal of the high-pass filter 85 should cause the deflection of the indicator 73 to attain a maximum for an optimal adjustment.

In a further modified embodiment relating to FIG. 5, the graticule or grid 80 is caused to vibrate, and only that light which is emitted by a small region, approximately to a point, of the output screen 15 is converted into an electrical signal, for example, by means of an image selector 70 as shown in FIG. 1. The vibrating graticule or grid 80 causes a modulation with respect to time of the electrical signal; thus the need for scanning by means of an image pick-up tube 75 can be dispensed with. The electrical signal thus generated can be processed in the described manner. The frequency of the squarewave-like reference voltage 86 will be determined by the frequency at which the graticule or grid 80 vibrates and also by the spatial construction of the graticule or grid 80. These considerations also apply to the choice of the cut-off frequency of the high-pass filter 85. The reference voltage 86 can alternatively be obtained by arranging a photodiode 95 on one side of the graticule or grid 80 and a light source 97 on the other. This is shown diagrammatically in FIG. 5.

The described methods and apparatus for performing the method claimed, can also be applied to other image intensifier chains which are used, for example, in infrared or low-light-level applications, or with γ-illumination.

What is claimed is:

1. A method of adjusting an image intensifier to obtain an optimum adjustment at least of a focussing voltage applied to the image intensifier comprising the steps of exposing the input screen of the image intensifier to input radiation, converting light originating from at least a portion of the output screen of the image intensifier into a first electrical signal, sensing the difference between said first signal and a reference value and adjusting said focussing voltage until said difference attains an extreme value.

2. A method as claimed in claim 1, for obtaining an optimum adjustment of both the focussing voltage and the focussing adjustment of an output objective located beyond the output screen of the image intensifier by iteration, in which the difference between the first signal and the reference value is adjusted to an extreme value during each of a plurality of iterations.

3. A method as claimed in claim 1, in which the input radiation is modulated as a function of location, and the output light thus produced is converted into a first signal which is amplitude modulated as a function of time.

4. Apparatus for carrying out the method claimed in claim 1 including an image pick-up tube, means for transferring the image on said output screen to said image pick-up tube, a non-linear amplifier arranged to amplify the output of said pick-up tube, an integrator which is connected thereto and an indicator for indicating the output of said integrator.

5. A method as claimed in claim 1 in which a noise signal is filtered from the first signal and adjustment is carried out until the absolute amplitude of said noise signal is maximized.

6. A method as claimed in claim 5, in which the noise signal is modified in a non-linear manner and is subsequently integrated.

7. A method as claimed in claim 1 in which the input radiation is modulated as a function of location and of time, and the light output thus produced is converted into an amplitude modulated first signal.

8. A method as claimed in claim 7 in which a reference value is formed in a manner consistent with the form of modulation applied to the input radiation, and said reference value is subtracted from said first signal, the adjustment of the image intensifier being carried out to minimize the difference between the first signal and the reference value.

9. A method as claimed in claim 7 in which the first signal is passed through a high-pass filter and the adjustment of the image intensifier chain is carried out so as to maximize the amplitude of the output signal from said filter.

10. A method as claimed in claim 1 in which said input radiation is X-radiation.

11. Apparatus for carrying out a method as claimed in claim 1 comprising an image selector, photo-electric means and a measuring instrument, the image selector including a lens system having a focal point which is arranged to coincide with an opaque wall forming part of said image selector, at least one aperture being present in said wall which is arranged between the lens system and said photo-electric means.

12. Apparatus as claimed in claim 11, in which there are provided a plurality of apertures in said opaque wall of said image selector, said apertures being situated at different distances from the optical axis, a non-linear amplifier being provided for each electrical signal respectively generated via each corresponding aperture, the output of the said amplifier being connected to a corresponding summation input of an adding unit.

13. Apparatus as claimed in claim 11 further including a differential amplifier and an nonlinear amplifier, the differential amplifier being connected between an output of the photoelectric means and an input of the nonlinear amplifier.

14. Apparatus as claimed in claim 13 in which a graticule is arranged in front of an image intensifier to serve as a modulator for the input radiation and the reference signal.

15. Apparatus as claimed in claim 11 further including a nonlinear amplifier and a high pass filter, the high pass filter being connected between an output of the photoelectric means and an input of the nonlinear amplifier.

16. Apparatus as claimed in claim 15 in which a graticule is arranged in front of an image intensifier to serve as a modulator for the input radiation and the reference signal.

17. Apparatus for adjusting an image intensifier to obtain an optimum adjustment of at least a focusing voltage comprising:
an image selector, photo-electric means and a measuring instrument, the image selector including a lens system having a focal point which is arranged to coincide with an opaque wall forming part of said image selector, at least one aperture being present in said wall which is arranged between the lens system and said photo-electric means.

18. Apparatus as claimed in claim 17 in which there are provided a plurality of apertures in said opaque wall of said image selector, said apertures being situated at different distances from an optical axis, a non-linear amplifier being provided for an electrical signal respectively generated through each corresponding aperture, the output of the said amplifier being connected to a corresponding summation input of an adding unit.

19. Apparatus for adjusting an electrically focused image intensifier comprising an image pickup tube, means for transferring the image on an output screen of said image intensifier to said image pickup tube, a nonlinear amplifier connected to amplify the output of said pickup tube, an integrator which is connected thereto and an indicator for indicating the output of said integrator.

20. Apparatus as claimed in claim 19 further comprising a high-pass filter connected between the output of the pickup tube and the input of the non-linear amplifier.

21. Apparatus as claimed in claim 20 further comprising a differential amplifier connected between an output of the pickup tube and the input of the non-linear amplifier.

22. Apparatus as claimed in claim 20 in which a graticule is disposed in front of an image intensifier as a modulator for the input radiation and the reference signal.

* * * * *